US00PP14012P29

(12) United States Plant Patent
Kraan

(10) Patent No.: US PP14,012 P2
(45) Date of Patent: Jul. 22, 2003

(54) ROSA PLANT NAMED 'BOKRAMAR'

(75) Inventor: Kees Jan Kraan, Boskoop (NL)

(73) Assignee: Boot and Company, Boskoop (NL)

( * ) Notice: Subject to any disclaimer, the term of this patent is extended or adjusted under 35 U.S.C. 154(b) by 0 days.

(21) Appl. No.: 10/121,161

(22) Filed: Apr. 11, 2002

(51) Int. Cl.[7] ..... A01H 5/00

(52) U.S. Cl. ..... Plt./102

(58) Field of Search ..... Plt./102

(56) References Cited

PUBLICATIONS

UPOV ROM GTITM Computer Database, GTI JOUVE Retrieval Software 2002/02, citation(s) for 'Bokramar'.*

* cited by examiner

*Primary Examiner*—Bruce R. Campell
*Assistant Examiner*—W C Haas
(74) *Attorney, Agent, or Firm*—Mark P. Bourgeois

(57) ABSTRACT

A new cultivar of Rosa plant named 'Bokramar' that is characterized by a low-growing habit, decreased susceptibility to disease, and pink flowers that gradually fade giving them a bi-colored appearance. In combination these traits set 'Bokramar' apart from all other existing varieties of Rosa known to the inventor.

1 Drawing Sheet

Botanical classification: Rosa.
Variety denomination: 'Bokramar'.

BACKGROUND OF THE INVENTION

The present invention relates to a new and distinct cultivar of Rose plant botanically known as Rosa and hereinafter referred to by the cultivar name 'Bokramar'.

The new cultivar is the product of a breeding program conducted by the inventor in a cultivated area of Boskoop, The Netherlands. The objectives of the breeding program were to develop a rose plant not exceeding one meter in height and exhibiting pink flowers that repeat flower. 'Bokramar' is a hybrid seedling that originated from the induced hybridization of the female or seed parent Rosa 'Ivtagolf' (U.S. Plant Pat. No. 11,371) and an unidentified male or pollen parent. The new cultivar 'Bokramar' was selected by the inventor in 1997 as a plant within the progeny of the stated cross in a controlled environment of Boskoop, The Netherlands.

The closest comparison plant is Rosa 'Mozart' (unpatented). 'Bokramar' is distinguishable from 'Mozart' by larger flowers, flower color, less vigor and shorter height. The new cultivar 'Bokramar' is distinguishable from the female parent Rosa 'Ivtagolf' by pink flowers, larger flowers and leaves that are larger in size and lighter green in color.

Asexual reproduction was accomplished by the inventor in 1998 using softwood cuttings in Boskoop, The Netherlands. Since that time, under careful observation, the unique characteristics of the new Rose cultivar have been uniform, stable and reproduced true to type in successive generations of asexual reproduction.

SUMMARY OF THE INVENTION

The following represent the distinguishing characteristics of the new Rosa cultivar 'Bokramar'. These traits in combination distinguish 'Bokramar' as a new and distinct cultivar apart from all other existing varieties of Rosa known to the inventor. 'Bokramar' has not been tested under all possible conditions and phenotypic differences may be observed with variations in environmental, climatic, and cultural conditions, however, without any variance in genotype.

1. Rosa 'Bokramar' exhibits strong-pink flowers that fade to a soft-pink, giving a bi-colored effect to the flowers.
2. Rosa 'Bokramar' is low-growing and does not exceed one meter in height at maturity.
3. Rosa 'Bokramar' exhibits repeat flowering.
4. Rosa 'Bokramar' is hardy to USDA Zone 6.
5. Rosa 'Bokramar' is less susceptible to disease than other Roses.

BRIEF DESCRIPTION OF THE DRAWING

The accompanying drawing illustrates the distinguishing traits of Rosa 'Bokramar'. The plant illustrated is three-years-old and was field grown in two-litre containers. The drawing on sheet 1 illustrates the foliage and flowers when in full bloom. The drawing was made using conventional techniques and although colors may appear ditterent from actual colors due to light reflectance, they are as accurate as possible by conventional photography.

BOTANICAL DESCRIPTION OF THE PLANT

The following is a detailed description of the Rosa cultivar named 'Bokramar'. Data was collected in Boskoop, The Netherlands from three-year-old field grown plants in two-litre containers. The time of year was July and the temperatures ranged from 14–24° Centigrade during the day, and 6–12° Centigrade during the night. The light level was natural outdoor light and there were no photoperiodic treatments or growth retardants used on the plants. Color determinations are in accordance with The Royal Horticultural Society Colour Chart except where general color terms of ordinary dictionary significance are used. The growing requirements are similar to the species.

Botanical classification: Rosa 'Bokramar'.
Type: Perennial.
Use: Ornamental shrub.

Parentage: 'Bokramar' is a hybrid plant that resulted from the induced hybridization of the following parent plants:
*Female parent.*—Rosa 'Ivtagolf' (U.S. Plant Pat. No. 11,371).
*Male parent.*—Unidentified rose.
Vigor: Moderate.
Growth rate: Approximately 15 cm. per month in spring.
Growth habit. Upright and broad.
Plant shape: Globose.
Suitable container size: 1–2 litre container.
Height: 1 meter in height.
Width: 1 meter in width.
Hardiness: USDA Zone 6.
Propagation: Softwood cuttings.
Time to initiate roots: Approximately 60 days are required to produce roots on an initial cutting.
Crop time: Approximately 14 months are required to achieve a finished plant from an unrooted cutting.
Root system: Fine and fibrous.
Light: Plant in full sun.
Soil: Plant in moist but well drained soil.
Seasonal interest: Pink flowers from late spring to autumn.
Stem:
*Branching habit.*—Basal branching and lateral branches with terminal inflorescences.
*Average number of lateral branches.*—Four.
*Stem diameter.*—Approximately 4 mm. in diameter.
*Stem length.*—Approximately 12 cm. in length.
*Stem strength.*—Strong.
*Stem color.*—143C.
*Pubescence.*—Absent.
*Internode length.*—Approximately 4.8 cm. between nodes.
*Shape.*—Cylindrical.
*Surface.*—Glabrous and dull and sparsely covered with sharp spines.
*Number of spines.*—0.25 per square cm.
*Spine dimensions.*—Approximately 5 mm. in length and 7 mm. in width.
*Color of spines.*—187A,B.
Foliage:
*Durability to foliage stresses.*—High.
*Texture.*—Smooth and glossy.
*Leaf arrangement.*—Alternate.
*Compound or single.*—Compound.
*Quantity of leaves per lateral branch.*—Approximately 17.
*Quantity of leaflets per leaf.*—Seven (5 near the inflorescence).
*Leaf margin.*—Serrate.
*Pubescence.*—Absent.
*Stipules.*—Present.
*Stipule dimensions.*—2.2 cm. in length and 2.5 mm. in width.
*Stipule color.*—144A.
*Stipule apex.*—Acuminate.
*Stipule margins.*—Lacerate.
*Vein pattern.*—Pinnate.
*Vein color* (*abaxial surface*).—144C.
*Vein color* (*adaxial surface*).—144B.
*Leaf shape.*—Ovate to elliptic.
*Leaf apex.*—Apiculate.
*Leaf base.*—Rounded.
*Leaf attachment.*—Petiolate.
*Petiole dimensions.*—3 cm. in length and 1.7 mm. in diameter.
*Petiole color.*—144B.
*Rachis color.*—143B.
*Other.*—Average of 6 sharp spines at base of rachis that are 2 mm. in length and 170B in color.
*Leaf length.*—11 cm. in length.
*Leaf width.*—8.5 cm. in width.
*Leaflet length.*—4.7 cm. in length.
*Leaflet width.*—2.6 cm. in width.
*Young leaf color* (*abaxial surface*).—144A.
*Young leaf color* (*adaxial surface*).—Closest to 143A but darker.
*Mature leaf color* (*abaxial surface*).—144A.
*Mature leaf color* (*adaxial surface*).—Closest to 137A but more yellow.
Flower:
*Flower arrangement.*—Compound terminal corymb.
*Inflorescence type.*—Compound terminal corymb.
*Inflorescence height.*—Approximately 25 cm. in height.
*Inflorescence diameter.*—Approximately 30 cm. in diameter.
*Quantity of flowers per inflorescence.*—Approximately 12.
*Flower type.*—Single.
*Flowering habit.*—Repeat flowering from late May to mid October.
*Quantity of flowers per lateral stem.*—Approximately 150.
*Quantity of flower buds per lateral stem.*—Approximately 150.
*Quantity of flowers and buds per plant.*—Approximately 600.
*Flowering season.*—Late spring to autumn.
*Time to flower* (*response time*).—Approximately 6 months.
*Rate of flower opening.*—Approximately 20% of the flowers per corymb are opened at once.
*Fragrance.*—Faint perfume scent.
*Flower bud length.*—1.4 cm. in length.
*Flower bud diameter.*—1.1 cm. in diameter.
*Flower bud shape.*—Broad ovate.
*Bud color.*—60A,B.
*Flower aspect.*—Upright to outward.
*Flower shape.*—Rotate.
*Flower dimensions.*—5.5 cm. in diameter and 1.8 cm. in height.
*Flower longevity.*—Lasts approximately 10 days on plant.
*Petal color when opening* (*under side*).—57A.
*Petal color when opening* (*upper side*).—57A.
*Petal color fully opened* (*upper side*).—66B.
*Petal color fully opened* (*under side*).—57A.
*Petal color fading to* (*upper and lower surface*).—Fading to 68B and then to 62C.
*Petal appearance.*—Dull.
*Petal texture.*—Glabrous.
*Petal arrangement.*—Rotate.
*Number of petals.*—Eight in number.
*Petals fused or unfused.*—Unfused.
*Petal shape.*—Broad obovate.
*Petal margin.*—Entire.
*Petal apex.*—Retuse.
*Petal dimensions.*—2.4 cm. in length and 2.5 cm. in width.
*Petaloids.*—Absent.
*Self-cleaning or persistent.*—Self-cleaning.
*Peduncle strength.*—Strong.

*Peduncle color.*—143C.
*Peduncle dimensions.*—6.5 cm. in length and 3.5 mm. in diameter.
*Peduncle angle.*—45–55°.
*Pedicels.*—Present.
*Pedicel dimensions.*—3 cm. in length and 1 mm. in diameter.
*Pedicel angle.*—0–70°.
*Pedicel color.*—Ranges from 143C to 174A.
*Sepal color* (*upper side*).—144B.
*Sepal color* (*under side*).—144A.
*Sepal surface.*—Dull and pubescent.
*Sepal arrangement.*—Rotate and reflexed.
*Number of sepals.*—Five.
*Sepal shape.*—Ovate.
*Sepal margin.*—Entire and can have pale green glandular hairs 0.2 mm in length, with a dark reddish brown gland on top.
*Sepal apex.*—Caudate.
*Sepal base.*—Broad cuneate.
*Sepal dimensions.*—1.6 cm. in length and 0.6 cm. in width.
*Calyx shape.*—Rotate and reflexed.
*Calyx dimensions.*—1.5 cm. in length and 1.2 cm. in diameter.

Reproduction organs:
*Stamen number.*—Approximately 100.
*Anther shape.*—Irregular kidney shape and curled.
*Anther attachment.*—Dorsifixed.
*Anther dimensions.*—1 mm. in diameter and 1 mm. in length.
*Anther color.*—24A.
*Amount of pollen.*—Low.
*Pollen color.*—14A.
*Pistil number.*—19 in number.
*Pistil dimensions.*—6 mm. in length and 1.5 mm. in diameter.
*Stigma shape.*—Irregular and flattened.
*Stigma color.*—144D.
*Style dimensions.*—5.2 mm. in length and 1.5 mm. in diameter.
*Style color.*—144D.
*Ovary color.*—143B.

Seed: Seed production has not been observed.

I claim:

1. A new and distinct variety of Rosa plant named 'Bokramar' as described and illustrated.

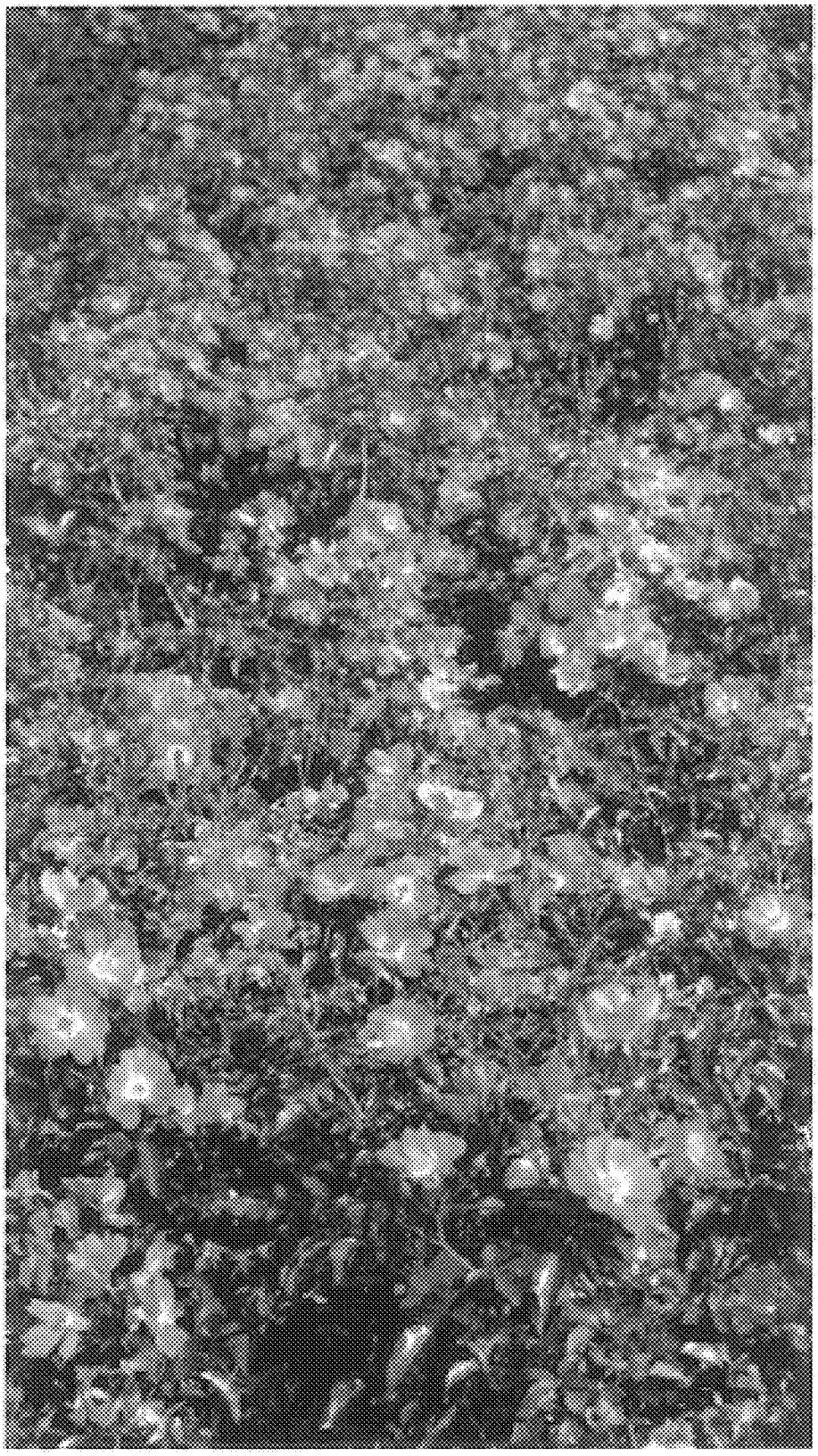

* * * * *